(12) United States Patent
Draa et al.

(10) Patent No.: US 12,229,834 B1
(45) Date of Patent: Feb. 18, 2025

(54) METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION

(71) Applicant: McKesson Corporation, Irving, TX (US)

(72) Inventors: Phillip Draa, Atlanta, GA (US); Jared Burdine, Dunwoody, GA (US); John Giglio, Brookhaven, GA (US)

(73) Assignee: MCKESSON CORPORATION, Irving, TX (US)

( * ) Notice: Subject to any disclaimer, the term of this patent is extended or adjusted under 35 U.S.C. 154(b) by 267 days.

(21) Appl. No.: 17/676,437

(22) Filed: Feb. 21, 2022

Related U.S. Application Data

(63) Continuation-in-part of application No. 16/792,413, filed on Feb. 17, 2020, now Pat. No. 11,610,240.

(51) Int. Cl.
*G06Q 30/00* (2023.01)
*G06Q 30/0283* (2023.01)
*G06Q 40/08* (2012.01)

(52) U.S. Cl.
CPC ......... *G06Q 40/08* (2013.01); *G06Q 30/0283* (2013.01)

(58) Field of Classification Search
CPC .......................... G06Q 40/08; G06Q 30/0283
See application file for complete search history.

(56) References Cited

U.S. PATENT DOCUMENTS

| | | | |
|---|---|---|---|
| 5,012,035 | A | 4/1991 | Sartori et al. |
| 5,173,851 | A | 12/1992 | Off et al. |
| 5,595,342 | A | 1/1997 | McNair et al. |
| (Continued) | | | |

FOREIGN PATENT DOCUMENTS

| | | |
|---|---|---|
| AU | 2003243327 A | 12/2003 |
| CA | 2 482 370 A1 | 3/2006 |
| (Continued) | | |

OTHER PUBLICATIONS

M. Bowman and S. Acharya, "Risk Assessment of Pharmacies & Electronic Prescriptions," 2019 IEEE/ACM International Conference on Advances in Social Networks Analysis and Mining (ASONAM), Vancouver, BC, Canada, 2019, pp. 641-644, doi: 10.1145/3341161.3343697. (Year: 2019) (Year: 2019).*

(Continued)

*Primary Examiner* — Sun M Li
(74) *Attorney, Agent, or Firm* — ALSTON & BIRD LLP

(57) ABSTRACT

A method, apparatus and computer program product are provided for partitioning prescription transaction costs in an electronic prescription transaction by determining a credit amount to be applied to an adjudicated prescription claim. The credit amount may be applied based on a co-pay amount provided by an adjudication computer and/or historical data, and may be adjusted according to an alternative cost obtained from an alternative cost data source. The alternative cost may be a cost for which a government sponsored plan can obtain the prescription. The remaining patient pay amount may be transmitted to a pharmacy computer such that a patient can purchase the prescription for a discounted cost.

15 Claims, 2 Drawing Sheets

(56) References Cited

U.S. PATENT DOCUMENTS

| | | |
|---|---|---|
| 5,628,530 A | 5/1997 | Thornton |
| 5,726,092 A | 3/1998 | Mathews et al. |
| 5,757,898 A | 5/1998 | Nishikawa |
| 5,769,228 A | 6/1998 | Wroblewski |
| 6,012,035 A | 1/2000 | Freeman et al. |
| 6,111,218 A | 8/2000 | Akers et al. |
| 6,463,462 B1 | 10/2002 | Smith et al. |
| 6,595,342 B1 | 7/2003 | Maritzen et al. |
| 6,726,092 B2 | 4/2004 | Goldberg et al. |
| 6,757,898 B1 | 6/2004 | Ilsen et al. |
| 6,769,228 B1 | 8/2004 | Mahar |
| 7,155,397 B2 | 12/2006 | Alexander et al. |
| 7,192,741 B2 | 3/2007 | Otte et al. |
| 7,337,129 B1 | 2/2008 | Lowry et al. |
| 7,346,768 B2 | 3/2008 | DiRienzo |
| 7,409,632 B1 | 8/2008 | DiRienzo |
| 7,426,476 B2 | 9/2008 | Munoz et al. |
| 7,734,483 B1 | 6/2010 | Smith et al. |
| 7,783,383 B2 | 8/2010 | Eliuk et al. |
| 7,840,424 B2 | 11/2010 | Wiley et al. |
| 7,856,364 B1 | 12/2010 | Wiley et al. |
| 7,912,741 B1 | 3/2011 | Pinsonneault |
| 7,921,021 B1 | 4/2011 | Newman |
| 8,036,913 B1 * | 10/2011 | Pinsonneault ......... G06Q 10/10 705/2 |
| 8,036,914 B1 | 10/2011 | Pinsonneault |
| 8,036,918 B1 | 10/2011 | Pinsonneault |
| 8,050,943 B1 | 11/2011 | Wiley et al. |
| 8,060,379 B1 | 11/2011 | Pinsonneault et al. |
| 8,126,743 B1 | 2/2012 | Wilk |
| 8,326,773 B1 | 12/2012 | Bellamy |
| 8,412,537 B1 | 4/2013 | Fenton et al. |
| 8,442,847 B1 | 5/2013 | Shrivastava |
| 8,489,415 B1 | 7/2013 | Ringold |
| 8,521,557 B1 | 8/2013 | Ringold et al. |
| 8,560,340 B1 | 10/2013 | Ringold |
| 8,645,162 B2 | 2/2014 | Boerger et al. |
| 8,671,018 B2 | 3/2014 | Thomas et al. |
| 8,712,797 B1 | 4/2014 | Bezdek et al. |
| 8,738,399 B1 | 5/2014 | Abou Nader et al. |
| 8,786,650 B1 | 7/2014 | Eller et al. |
| 8,799,018 B1 | 8/2014 | Rea et al. |
| 8,984,059 B2 | 3/2015 | Johnson |
| 9,026,507 B2 | 5/2015 | Shraim et al. |
| 9,100,793 B2 | 8/2015 | Johnson |
| 9,171,322 B2 | 10/2015 | Spievak et al. |
| 9,356,947 B2 | 5/2016 | Shraim et al. |
| 9,760,871 B1 | 9/2017 | Pourfallah et al. |
| 9,786,023 B2 | 10/2017 | Cohan et al. |
| 10,109,027 B1 | 10/2018 | Stack |
| 10,157,262 B1 | 12/2018 | Pinsonneault |
| 10,331,855 B1 * | 6/2019 | Bratton ................. G16H 20/00 |
| 10,417,380 B1 | 9/2019 | Kaye et al. |
| 10,489,552 B2 | 11/2019 | Pinsonneault |
| 10,496,793 B1 | 12/2019 | Lawrence et al. |
| 10,565,656 B1 | 2/2020 | Pinsonneault et al. |
| 10,606,984 B1 | 3/2020 | Kaye et al. |
| 10,616,146 B1 | 4/2020 | Hopkins et al. |
| 10,628,797 B2 | 4/2020 | Shraim et al. |
| 10,642,812 B1 | 5/2020 | Hopkins et al. |
| 10,713,694 B1 * | 7/2020 | Harris .................... G06Q 50/22 |
| 10,747,848 B2 | 8/2020 | Guinan |
| 10,778,618 B2 | 9/2020 | Karnin et al. |
| 10,862,832 B1 | 12/2020 | Harris |
| 10,924,545 B2 | 2/2021 | Momchilov et al. |
| 10,924,585 B1 | 2/2021 | Harris et al. |
| 10,929,932 B1 | 2/2021 | Golden et al. |
| 10,978,198 B1 | 4/2021 | Pinsonneault |
| 10,999,224 B1 | 5/2021 | Frechen et al. |
| 11,043,293 B1 | 6/2021 | Salzbrenner |
| 11,443,835 B1 | 9/2022 | Gangaikondan-Iyer et al. |
| 11,508,471 B1 | 11/2022 | Anselmi et al. |
| 2001/0029483 A1 | 10/2001 | Schultz et al. |
| 2001/0037216 A1 | 11/2001 | Oscar et al. |
| 2001/0039589 A1 | 11/2001 | Aho et al. |
| 2001/0056359 A1 | 12/2001 | Abreu |
| 2002/0002495 A1 | 1/2002 | Ullman |
| 2002/0004812 A1 | 1/2002 | Motoyama |
| 2002/0032582 A1 | 3/2002 | Feeney et al. |
| 2002/0032583 A1 | 3/2002 | Joao |
| 2002/0035484 A1 | 3/2002 | McCormick |
| 2002/0087583 A1 | 7/2002 | Morgan et al. |
| 2002/0111832 A1 | 8/2002 | Judge |
| 2002/0133379 A1 | 9/2002 | Lewis et al. |
| 2002/0143579 A1 | 10/2002 | Docherty et al. |
| 2002/0147614 A1 | 10/2002 | Doerr et al. |
| 2002/0188552 A1 | 12/2002 | Kavounas et al. |
| 2002/0198831 A1 | 12/2002 | Patricelli et al. |
| 2003/0009367 A1 | 1/2003 | Morrison |
| 2003/0050796 A1 | 3/2003 | Baldwin |
| 2003/0050799 A1 | 3/2003 | Jay et al. |
| 2003/0069760 A1 | 4/2003 | Gelber |
| 2003/0074234 A1 | 4/2003 | Stasny |
| 2003/0097310 A1 | 5/2003 | Ono et al. |
| 2003/0130875 A1 | 7/2003 | Hawash et al. |
| 2003/0149625 A1 | 8/2003 | Leonardi et al. |
| 2003/0154163 A1 | 8/2003 | Phillips et al. |
| 2003/0172008 A1 | 9/2003 | Hage et al. |
| 2003/0187690 A1 | 10/2003 | Miller |
| 2003/0229540 A1 | 12/2003 | Algiene |
| 2003/0236747 A1 | 12/2003 | Sager |
| 2004/0006490 A1 | 1/2004 | Gingrich et al. |
| 2004/0039599 A1 | 2/2004 | Fralic |
| 2004/0054685 A1 | 3/2004 | Rahn et al. |
| 2004/0059607 A1 | 3/2004 | Ball et al. |
| 2004/0073456 A1 | 4/2004 | Gottlieb et al. |
| 2004/0073457 A1 * | 4/2004 | Kalies .................... G16H 20/10 705/2 |
| 2004/0078222 A1 | 4/2004 | Khan et al. |
| 2004/0078234 A1 | 4/2004 | Tallal, Jr. |
| 2004/0088187 A1 | 5/2004 | Chudy et al. |
| 2004/0103062 A1 | 5/2004 | Wood et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0199545 A1 | 10/2004 | Wagner et al. |
| 2004/0236630 A1 | 11/2004 | Kost et al. |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0065821 A1 | 3/2005 | Kalies, Jr. |
| 2005/0075932 A1 | 4/2005 | Mankoff |
| 2005/0080692 A1 | 4/2005 | Padam et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240442 A1 | 10/2005 | Lapsker et al. |
| 2005/0240473 A1 | 10/2005 | Ayers, Jr. et al. |
| 2005/0261939 A1 | 11/2005 | Augspurger et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0036470 A1 * | 2/2006 | Oaks ..................... G16H 20/10 705/2 |
| 2006/0085231 A1 | 4/2006 | Brofman |
| 2006/0085385 A1 | 4/2006 | Foster et al. |
| 2006/0113376 A1 | 6/2006 | Reed et al. |
| 2006/0149595 A1 | 7/2006 | Williams et al. |
| 2006/0149784 A1 | 7/2006 | Tholl et al. |
| 2006/0184391 A1 | 8/2006 | Barre et al. |
| 2006/0212318 A1 | 9/2006 | Dooley |
| 2006/0212345 A1 | 9/2006 | Soza et al. |
| 2006/0224414 A1 | 10/2006 | Astrup et al. |
| 2006/0224417 A1 | 10/2006 | Werner |
| 2006/0224443 A1 | 10/2006 | Soza et al. |
| 2006/0235747 A1 | 10/2006 | Hammond et al. |
| 2006/0259363 A1 | 11/2006 | Jhetam et al. |
| 2007/0005402 A1 | 1/2007 | Kennedy et al. |
| 2007/0033137 A1 | 2/2007 | Provost et al. |
| 2007/0043589 A1 | 2/2007 | Warren et al. |
| 2007/0043595 A1 | 2/2007 | Pederson |
| 2007/0050209 A1 | 3/2007 | Yered |

(56) References Cited

U.S. PATENT DOCUMENTS

| | | |
|---|---|---|
| 2007/0050210 A1* | 3/2007 | Wiley, II ............... G06Q 30/06 705/2 |
| 2007/0067186 A1 | 3/2007 | Brenner et al. |
| 2007/0094133 A1 | 4/2007 | Anandarao et al. |
| 2007/0108053 A1 | 5/2007 | Cramer et al. |
| 2007/0136100 A1 | 6/2007 | Daugherty et al. |
| 2007/0162303 A1 | 7/2007 | Wiley et al. |
| 2007/0168228 A1 | 7/2007 | Lawless |
| 2007/0185799 A1 | 8/2007 | Harrison et al. |
| 2007/0191985 A1 | 8/2007 | Bain |
| 2007/0194352 A1 | 8/2007 | Han |
| 2007/0202886 A1 | 8/2007 | Dhebri et al. |
| 2007/0204043 A1 | 8/2007 | Espinosa et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |
| 2007/0260750 A1 | 11/2007 | Feied et al. |
| 2007/0276697 A1 | 11/2007 | Wiley et al. |
| 2007/0294765 A1 | 12/2007 | Rihn et al. |
| 2007/0299915 A1 | 12/2007 | Shraim et al. |
| 2008/0033750 A1 | 2/2008 | Swiss et al. |
| 2008/0103836 A1 | 5/2008 | Park et al. |
| 2008/0112411 A1 | 5/2008 | Stafford et al. |
| 2008/0152107 A1 | 6/2008 | Mendiola |
| 2008/0183492 A1 | 7/2008 | Warren et al. |
| 2008/0215361 A1 | 9/2008 | Nunnari et al. |
| 2008/0262948 A1 | 10/2008 | Grady et al. |
| 2009/0006141 A1 | 1/2009 | Karr |
| 2009/0030719 A1 | 1/2009 | Nadas et al. |
| 2009/0064330 A1 | 3/2009 | Shraim et al. |
| 2009/0083064 A1 | 3/2009 | Mahinda |
| 2009/0094051 A1 | 4/2009 | Ard et al. |
| 2009/0100099 A1 | 4/2009 | Buckwalter |
| 2009/0106313 A1 | 4/2009 | Boldyga |
| 2009/0112707 A1 | 4/2009 | Weiss et al. |
| 2009/0198510 A1 | 8/2009 | Ditto |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0287001 A1 | 11/2010 | Pearce et al. |
| 2010/0293236 A1 | 11/2010 | Wisner et al. |
| 2011/0015978 A1 | 1/2011 | Welch, Jr. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1* | 10/2012 | John ....................... G16H 40/67 705/2 |
| 2012/0265591 A1 | 10/2012 | Hwang |
| 2012/0323608 A1 | 12/2012 | Herzlinger |
| 2013/0041968 A1 | 2/2013 | Cohen et al. |
| 2013/0046610 A1 | 2/2013 | Abraham |
| 2013/0103602 A1 | 4/2013 | Melnick et al. |
| 2013/0144715 A1 | 6/2013 | Kranzley et al. |
| 2013/0179180 A1 | 7/2013 | Patra |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278448 A1 | 9/2014 | Sadeghi et al. |
| 2014/0278456 A1 | 9/2014 | Milosevich et al. |
| 2014/0278531 A1 | 9/2014 | Gupta |
| 2015/0032465 A1 | 1/2015 | Sundar et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1 | 9/2015 | Pinsonneault et al. |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0103978 A1 | 4/2016 | Stong |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0321406 A1 | 11/2016 | Timmerman et al. |
| 2016/0321410 A1 | 11/2016 | Timmerman et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1 | 11/2017 | Kranzley et al. |
| 2017/0324695 A1 | 11/2017 | Fischer et al. |
| 2017/0329922 A1 | 11/2017 | Eberting et al. |
| 2018/0012244 A1 | 1/2018 | Leonardi |
| 2018/0366810 A1 | 12/2018 | Nero et al. |
| 2019/0095582 A1 | 3/2019 | Waits |
| 2019/0213212 A1 | 7/2019 | Adato et al. |
| 2019/0252049 A1 | 8/2019 | Fotsch et al. |
| 2019/0385733 A1 | 12/2019 | Kaye et al. |
| 2019/0385734 A1 | 12/2019 | Pinsonneault |
| 2020/0105392 A1 | 4/2020 | Karkazis et al. |
| 2020/0372988 A1 | 11/2020 | Bezdek et al. |
| 2021/0319887 A1 | 10/2021 | Derrick, Jr. et al. |
| 2021/0374876 A1 | 12/2021 | Cedergreen |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 A1 | 5/1991 |
| WO | WO 1995/003569 A2 | 2/1995 |
| WO | WO 1997/025682 A1 | 7/1997 |
| WO | WO 1998/050871 A1 | 11/1998 |
| WO | WO 2000/039737 A1 | 7/2000 |
| WO | WO 2003/098401 A2 | 11/2003 |
| WO | WO 2007/025295 A2 | 3/2007 |

(56) References Cited

FOREIGN PATENT DOCUMENTS

| WO | WO 2007/094772 A1 | 8/2007 |
|---|---|---|
| WO | WO 2008/092109 A2 | 7/2008 |

OTHER PUBLICATIONS

C. Gemmil, M. (2008). The price elasticity of demand for prescription drugs: an exploration of demand in different settings (Order No. U615895). Available from ProQuest Dissertations and Theses Professional. (1625984575). (Year: 2008) (Year: 2008).*
S. Liu, J. C. Xu, G. Liu, H. Xue, D. Bishai and Y. Wang, "Evaluating Cost-Effectiveness of Treatment Options for Diabetes Patients Using System Dynamics Modeling," 2018 Winter Simulation Conference (WSC), Gothenburg, Sweden, 2018, pp. 2577-2588, doi: 10.1109/WSC.2018.8632264. (Year: 2018).*
Tiriveedhi V. Impact of Precision Medicine on Drug Repositioning and Pricing: a too Small to Thrive Crisis. J Pers Med. Nov. 5, 2018;8(4):36. doi: 10.3390/jpm8040036. PMID: 30400625; PMCID: PMC6313451. (Year: 2018).*
Dubois, Robert W., "Rx Drug Costs: List Prices Versus Net Prices and the Importance of Staying Within the Data", Health Affairs Blog, Mar. 2019, 7 pages.
Kamal, Rabah, et al., "What are the recent and forecasted trends in prescription drug spending?" Peterson-KFF Health System Tracker, Feb. 20, 2019, 19 pages, Peterson Center on Healthcare.
Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.
United States Patent and Trademark Office, Final Office Action received for U.S. Appl. No. 16/867,286, dated Sep. 8, 2022, 19 pages, U.S.
United States Patent and Trademark Office, Notice of Allowance received for U.S. Appl. No. 16/792,413, dated Sep. 8, 2022, 18 pages, U.S.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Final Office Action received for U.S. Appl. No. 17/175,939, dated Oct. 5, 2022, 30 pages, U.S.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.
"Pharmacy Reject Codes" NCPDP, 5 pages.
"St. Vincent's first to use Birmingham startup's information system." the Birmingham News [Online] Apr. 11, 2005. URL: http://www.awarix.com.
"St. Vincent's is Digital Flagship" D. Lockridge; Birmingham Medical News [Online] Sep. 2005.
"Two automatic identification technology, neither new in the sense if being recent developments . . . " Patient Safety & Quality Healthcare [Online] Aug. 2005_ URL: http://www_awarix.com.
Advisory Action for U.S. Appl. No. 14/193,294 mailed Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Advisory Action for U.S. Appl. No. 15/137,371 mailed Feb. 25, 2019, 5 pages.
Advisory Action for U.S. Appl. No. 15/427,746 mailed Jul. 2, 2019, 2 pages.
Advisory Action received for U.S. Appl. No. 15/085,166, dated Jan. 29, 2021, 3 pages, US.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central LTD, UK.
CMS Updates Drug Dashboards with Prescription Drug Pricing and Spending Data, Data, Medicare Part D, Prescription drugs (Mar. 14, 2019).
Consalvo, Bob; "City of Boston in the City Council" hearing notice, Dec. 6, 2006.
Coping with Information Overload. The News Source for Healthcare Information Technology [Online] Nov. 2004. URL: http://www.awarix.com.
Decision to Grant European Patent Application No. 13809457.8 dated May 18, 2017.
Examiner's Answer for U.S. Appl. No. 14/145,027 mailed Sep. 7, 2016, 27 pages.
Extended European Search Report for European Application No. 13809457.8 dated Apr. 15, 2016, 6 pages.
Final Office Action for U.S. Appl. No. 12/140,015 mailed Jan. 31, 2011, 10 pages.
Final Office Action for U.S. Appl. No. 12/415,062 mailed Oct. 6, 2011, 18 pages.
Final Office Action for U.S. Appl. No. 12/555,589 mailed Apr. 11, 2012, 17 pages.
Final Office Action for U.S. Appl. No. 12/560,071 mailed Aug. 28, 2015, 8 pages.
Final Office Action for U.S. Appl. No. 12/560,071 mailed Nov. 8, 2012, 11 pages.
Final Office Action for U.S. Appl. No. 12/570,982 mailed Apr. 11, 2014, 22 pages.
Final Office Action for U.S. Appl. No. 12/570,982 mailed Aug. 28, 2015, 10 pages.
Final Office Action for U.S. Appl. No. 12/570,982 mailed Jan. 17, 2013, 19 pages.
Final Office Action for U.S. Appl. No. 12/730,015 mailed Aug. 14, 2012, 10 pages.
Final Office Action for U.S. Appl. No. 12/978,898 mailed May 16, 2013, 16 pages.
Final Office Action for U.S. Appl. No. 13/721,890 mailed Jun. 24, 2015, 14 pages.
Final Office Action for U.S. Appl. No. 13/721,890 mailed Nov. 25, 2016, 12 pages.
Final Office Action for U.S. Appl. No. 13/782,909 mailed May 31, 2016, 18 pages.
Final Office Action for U.S. Appl. No. 13/782,909 mailed Oct. 6, 2015, 24 pages.
Final Office Action for U.S. Appl. No. 13/804,175 mailed Oct. 6, 2015, 6 pages.
Final Office Action for U.S. Appl. No. 13/827,676 mailed Jul. 13, 2015, 17 pages.
Final Office Action for U.S. Appl. No. 14/090,113 mailed Jan. 6, 2016, 18 pages.
Final Office Action for U.S. Appl. No. 14/090,122 mailed Apr. 22, 2016, 13 pages.

(56) References Cited

OTHER PUBLICATIONS

Final Office Action for U.S. Appl. No. 14/145,027 mailed Nov. 19, 2015, 12 pages.
Final Office Action for U.S. Appl. No. 14/193,294 mailed May 2, 2016, 29 pages.
Final Office Action for U.S. Appl. No. 14/218,326 mailed Jun. 30, 2016, 17 pages.
Final Office Action for U.S. Appl. No. 15/085,166, dated Dec. 4, 2020, 11 pages.
Final Office Action for U.S. Appl. No. 15/137,371 mailed Nov. 28, 2018, 24 pages.
Final Office Action for U.S. Appl. No. 15/427,746 mailed Apr. 15, 2019, 9 pages.
Google NPL (non-patent literature) Search on "pharmacy payment benefit copay NDC database", retrieved from the Internet at <https://scholar.google.com/scholar?hl=en&as_sdt=3,47&g=pharmacy+payment+benefit+copay+NDC+database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.
Google Patents Search (including Web Search History, Prior Art Search Printable History Generator) on "pharmacy payment benefit copay NDC database) (prescription) (code) (refills) (error code) country:US before:filing:20131231", retrieved from the Internet at <https://patents.google.com/?q=pharmacy+payment+benefit+copay+NDC+database&q=prescription&q=code&q=refills&q=error+code&country=US&before=filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt=0%2C47&as_ylo=2010&as_yhi=2013&q=pharmacy+payment+benefit+copay+NDC+database+pres . . . > retrieved on Jun. 1, 2022, 3 pages.
How to Estimate the Cost of a Prescription. Pam Olson, Sr. Client Services Executive, Navitus Health Solutions (Year: 2015).
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-Prescriptions, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 mailed Jan. 14, 2015, 11 pages.
Marie Chisholm et al. "Pharmaceutical Manufacturer Assistance Program." Arch Intern Med. Vol. 162, Apr. 8, 2002.
Non-Final Office Action for U.S. Appl. No. 12/560,071 mailed Jun. 21, 2012, 11 pages.
Non-Final Office Action for U.S. Appl. No. 12/570,982 mailed Jun. 20, 2012, 10 pages.
Non-Final Office Action for U.S. Appl. No. 14/193,294 mailed Feb. 21, 2017, 32 pages.
Non-Final Office Action for U.S. Appl. No. 15/085,166 dated Jun. 12, 2020, 26 pages.
Non-Final Office Action for U.S. Appl. No. 16/180,915 dated Jun. 1, 2020, 40 pages.
Non-final Office Action for U.S. Appl. No. 12/140,015 mailed Oct. 8, 2010, 9 pages.
Non-final Office Action for U.S. Appl. No. 12/189,650 mailed Jan. 22, 2010, 11 pages.
Non-final Office Action for U.S. Appl. No. 12/189,654 mailed Jan. 22, 2010, 11 pages.
Non-Final Office Action for U.S. Appl. No. 12/388,956 mailed Feb. 3, 2011, 11 pages.
Non-Final Office Action for U.S. Appl. No. 12/415,062 mailed Mar. 30, 2011, 23 pages.
Non-Final Office Action for U.S. Appl. No. 12/555,589 mailed Dec. 9, 2011, 12 pages.
Non-Final Office Action for U.S. Appl. No. 12/560,071 mailed Sep. 23, 2014, 17 pages.
Non-Final Office Action for U.S. Appl. No. 12/570,982 mailed Sep. 12, 2013, 22 pages.
Non-Final Office Action for U.S. Appl. No. 12/730,015 mailed Mar. 6, 2012, 9 pages.
Non-Final Office Action for U.S. Appl. No. 12/956,411 mailed Jan. 24, 2011, 9 pages.
Non-Final Office Action for U.S. Appl. No. 12/978,898 mailed Feb. 6, 2013, 12 pages.
Non-Final Office Action for U.S. Appl. No. 12/982,395 mailed Dec. 11, 2012, 13 pages.
Non-Final Office Action for U.S. Appl. No. 13/721,890 mailed Jan. 9, 2015, 11 pages.
Non-Final Office Action for U.S. Appl. No. 13/721,890 mailed Jun. 14, 2016, 9 pages.
Non-final Office Action for U.S. Appl. No. 13/782,909 mailed Feb. 11, 2016, 17 pages.
Non-Final Office Action for U.S. Appl. No. 13/827,676 mailed Dec. 26, 2014, 13 pages.
Non-final Office Action for U.S. Appl. No. 13/827,676 mailed Dec. 30, 2015, 23 pages.
Non-Final Office Action for U.S. Appl. No. 14/145,027 mailed Mar. 23, 2015, 13 pages.
Non-Final Office Action for U.S. Appl. No. 15/137,371 mailed May 29, 2018, 19 pages.
Non-Final Office Action for U.S. Appl. No. 15/427,746 mailed Oct. 18, 2018, 9 pages.
Non-Final Office Action for U.S. Appl. No. 16/819,258 dated Sep. 4, 2020, 6 pages.
Non-Final Office Action received for U.S. Appl. No. 15/085,166, dated Mar. 17, 2021, 11 pages.
Non-Final Office Action received for U.S. Appl. No. 16/551,962, dated Mar. 2, 2021, 16 pages.
Non-Final Office Action received for U.S. Appl. No. 16/453,509 mailed Mar. 26, 2021, 45 pages.
Non-Final Office Action received for U.S. Appl. No. 16/832,318 mailed Apr. 23, 2021, 52 pages.
Notice of Allowance and Fees(s) Due for U.S. Appl. No. 15/925,011 dated Jan. 22, 2021, 15 pages.
Notice of Allowance for U.S. Appl. No. 16/180,915 dated Dec. 11, 2020, 23 pages.
Notice of Allowance for U.S. Appl. No. 11/674,069 mailed Jul. 19, 2010, 13 pages.
Notice of Allowance for U.S. Appl. No. 12/140,015 mailed Jun. 10, 2011, 10 pages.
Notice of Allowance for U.S. Appl. No. 12/165,221 mailed Nov. 16, 2010, 6 pages.
Notice of Allowance for U.S. Appl. No. 12/189,650 mailed Aug. 13, 2010, 11 pages.
Notice of Allowance for U.S. Appl. No. 12/388,956 mailed Jun. 14, 2011, 9 pages.
Notice of Allowance for U.S. Appl. No. 12/956,411 mailed Aug. 5, 2011, 8 pages.
Notice of Allowance for U.S. Appl. No. 12/982,395 mailed Apr. 24, 2013, 9 pages.
Notice of Allowance for U.S. Appl. No. 14/181,011 dated May 15, 2019, 9 pages.
Notice of Allowance for U.S. Appl. No. 15/137,371 mailed May 2, 2019, 11 pages.
Notice of Allowance for U.S. Appl. No. 15/427,746 mailed Dec. 4, 2019, 5 pages.
Notice of Allowance for U.S. Appl. No. 15/427,746 mailed Jul. 31, 2019, 8 pages.
Notice of Allowance received for U.S. Appl. No. 14/643,468, Oct. 24, 2018, 22 pages.
Notice of Allowance received for U.S. Appl. No. 14/181,011, filed Feb. 13, 2019, 9 pages.

(56) References Cited

OTHER PUBLICATIONS

Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/193,294 dated Sep. 19, 2018, 27 pages.
Office Action for U.S. Appl. No. 14/229,043 dated Feb. 27, 2019, 18 pages.
Office Action for U.S. Appl. No. 14/229,043 dated Jul. 24, 2017, 19 pages.
Office Action for U.S. Appl. No. 14/229,043 dated Sep. 5, 2019, 22 pages.
Office Action for U.S. Appl. No. 14/229,043 dated Sep. 14, 2018, 17 pages.
Office Action for U.S. Appl. No. 14/643,468 dated Mar. 8, 2018, 11 pages.
Office Action for U.S. Appl. No. 15/085,166 dated Dec. 27, 2018, 24 pages.
Office Action for U.S. Appl. No. 15/085,166 dated Jun. 29, 2018, 19 pages.
Office Action for U.S. Appl. No. 15/085,166 dated Mar. 3, 2020, 25 pages.
Office Action for U.S. Appl. No. 15/085,166 dated Sep. 4, 2019, 23 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
Office Action for U.S. Appl. No. 12/570,982 mailed Apr. 8, 2015, 9 pages.
Office Action for U.S. Appl. No. 13/782,909 mailed Jun. 25, 2015, 16 pages.
Office Action for U.S. Appl. No. 13/804,175 mailed Mar. 13, 2015, 9 pages.
Office Action for U.S. Appl. No. 14/090,113 mailed Jun. 18, 2015, 14 pages.
Office Action for U.S. Appl. No. 14/090,122 mailed Oct. 21, 2016, 12 pages.
Office Action for U.S. Appl. No. 14/090,122 mailed Sep. 11, 2015, 10 pages.
Office Action for U.S. Appl. No. 14/181,011 mailed Feb. 29, 2016, 23 pages.
Office Action for U.S. Appl. No. 14/181,011 mailed Mar. 20, 2017, 28 pages.
Office Action for U.S. Appl. No. 14/181,011 mailed Oct. 20, 2016, 28 pages.
Office Action for U.S. Appl. No. 14/181,011 mailed Sep. 12, 2017, 17 pages.
Office Action for U.S. Appl. No. 14/193,294 mailed Dec. 17, 2015, 21 pages.
Office Action for U.S. Appl. No. 14/218,326 mailed Dec. 1, 2015, 13 pages.
Opar, Alisa; "Rising drug costs prompt new uses for old pills." Nature Medicine, 1211333 (2006).
PTAB Decision on Appeal for U.S. Appl. No. 14/145,027 mailed May 31, 2018, 11 pages.
PTAB Decision on Request for Rehearing for U.S. Appl. No. 14/145,027 mailed Aug. 30, 2018, 9 pages.
Sampson, R.J., Taking Control of Health Care Costs, Best's Review—Life Health Insurance Edition, Nov. 1983, vol. 84, Issue 7, USA; Abstract only.
Scientific and Technical Information Center, Report of Information from Dialog (NPL (non-patent literature) Search Results, Abstracts only), dated Nov. 1, 2021, (Year: 2021), 9 pages.
Siler, Sharon et al., "Safe Disposal of Unused Controlled Substances" Avalere Health 2008.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
Supplemental Notice of Allowability received for U.S. Appl. No. 16/180,915, dated Jan. 28, 2021, 2 pages.
Supplemental Notice of Allowability received for U.S. Appl. No. 16/180,915, dated Mar. 12, 2021, 10 pages.
U.S. Notice of Allowance received for U.S. Appl. No. 16/819,258, dated Nov. 16, 2020, 8 pages, U.S.
U.S. Appl. No. 14/229,043, "Systems and Methods for Monitoring and Reporting Redemption Information at a Pharmacy for Patient Incentive Information Identified at the Time of Prescribing," Unpublished (Filed Mar. 28, 2014), (Roger Pinsonneault, Inventor), (McKesson Corporation, Assignee), abandoned.
U.S. Appl. No. 15/084,034, "Prescription Provider System," Unpublished (Filed Mar. 29, 2016), (Scott Genone, Inventor), (McKesson Corporation, Assignee), abandoned.
U.S. Appl. No. 15/085,166, "Alternative Therapy Identification System", Unpublished (Filed Mar. 30, 2016), (Elizabeth Kaye, Inventor), (McKesson Corporation, Assignee), pending.
U.S. Appl. No. 16/832,318, "Method, Apparatus, and Computer Program Product for Estimated Prescription Costs", Unpublished (Filed Mar. 27, 2020), (Stacy Hopkins, Inventor), (McKesson Corporation, Assignee), pending.
U.S. Appl. No. 17/012,565, "Method, Apparatus, and Computer Program Product for Performing an Alternative Evaluation Procedure in Response to an Electronic Message," Unpublished (filing date Sep. 4, 2020), (Stacy Hopkins, et al., Inventors) (McKesson Corporation, Assignee), pending.
U.S. Appl. No. 17/092,705, "Computing System and Method for Automatically Reversing an Action Indicated by an Electronic Message," Unpublished (filing date Nov. 9, 2020), (Patrick Harris, Inventor) (McKesson Corporation, Assignee), pending.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee), pending.
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee), pending.
U.S. Appl. No. 17/175,939, "Method, Apparatus, and Computer Program Product for Generating Inquiries in Different Formats, and Compiling Different Information Types in a Response," Unpublished (filed Feb. 15, 2021), (Stacy Hopkins, et al., Inventor) (McKesson Corporation, Assignee), pending.
U.S. Appl. No. 16/453,509, "Method, Apparatus, and Computer Program Product for Providing Estimated Prescription Costs," Unpublished (filed Jun. 26, 2019), (Stacy Hopkins, et al., Inventor) (McKesson Corporation, Assignee), pending.
U.S. Appl. No. 17/499,976, "Method, Apparatus, and Computer Program Product for Providing Real-Time Pricing Information," Unpublished (filed Oct. 13, 2021), (Stacy Hopkins, et al., Inventor) (McKesson Corporation, Assignee), pending.
U.S. Appl. No. 17/501,532, "Method, Apparatus, and Computer Program Product for Providing Real-Time Pricing Information," Unpublished (filed Oct. 14, 2021), (Keith Crozier, et al., Inventor) (McKesson Corporation, Assignee), pending.

(56) References Cited

OTHER PUBLICATIONS

U.S. Appl. No. 17/219,526, "Method and Apparatus for Parsing and Differently Processing Different Portions of a Request," Unpublished (filed Mar. 31, 2021), (Melissa Frechen, et al., Inventor) (McKesson Corporation, Assignee), pending.
U.S. Appl. No. 17/162,461, "Method, Apparatus, and Computer Program Product for Constructing Electronic Message Responses Dependent Upon Historical Information," Unpublished (filed Jan. 19, 2021), (Stewart Aragon, et al., Inventor) (McKesson Corporation, Assignee), pending.
U.S. Appl. No. 17/144,426, "Method, Apparatus, and Computer Program Product for Estimating a Target Quantitative Measure Based Upon Historical Electronic Messages," Unpublished (filed Jan. 8, 2021), (Stewart Aragon, et al., Inventor) (McKesson Corporation, Assignee), pending.
U.S. Appl. No. 17/158,118, "Method, Apparatus, and Computer Program Product for Estimating a Target Quantitative Measure Based Upon Historical Electronic Messages," Unpublished (filed Jan. 26, 2021), (Stewart Aragon, et al., Inventor) (McKesson Corporation, Assignee), pending.
U.S. Appl. No. 17/675,616, "Method, Apparatus, and Computer Program Product for Reformatting an Electronic Prescription Transaction," Unpublished (filed Feb. 18, 2022), (Phillip Draa, et al., Inventor) (McKesson Corporation, Assignee), pending.
U.S. Appl. No. 17/705,919, "Method, Apparatus, and Computer Program Product for Generating Alternative Evaluation Messages," Unpublished (filed Mar. 28, 2022), (Stacy Hopkins, et al., Inventor) (McKesson Corporation, Assignee), pending.
United States Patent and Trademark Office, Advisory Action for U.S. Appl. No. 15/422,184, filed Jun. 25, 2019, 4 pages, U.S.A.
United States Patent and Trademark Office, Advisory Action for U.S. Appl. No. 15/422,184, filed Mar. 26, 2020, 5 pages, U.S.A.
United States Patent and Trademark Office, Advisory Action for U.S. Appl. No. 15/925,011, filed Jan. 31, 2020, 3 pages, U.S.A.
United States Patent and Trademark Office, Advisory Action for U.S. Appl. No. 15/925,948, filed Jan. 31, 2020, 4 pages, U.S.A.
United States Patent and Trademark Office, Advisory Action received for U.S. Appl. No. 16/453,509, dated Oct. 12, 2021, 5 pages, U.S.
United States Patent and Trademark Office, Advisory Action received for U.S. Appl. No. 16/832,318, dated Jan. 28, 2022, 4 pages, U.S.
United States Patent and Trademark Office, Advisory Action received for U.S. Appl. No. 16/792,413, dated Mar. 10, 2022, 4 pages, US.
United States Patent and Trademark Office, Corrected Notice of Allowability received for U.S. Appl. No. 15/085,166, dated Sep. 20, 2021, 6 pages, U.S.
United States Patent and Trademark Office, Final Office Action received for U.S. Appl. No. 16/453,509, dated Aug. 18, 2021, 16 pages, U.S.
United States Patent and Trademark Office, Final Office Action received for U.S. Appl. No. 16/551,962, dated Nov. 4, 2021, 32 pages, U.S.
United States Patent and Trademark Office, Final Office Action received for U.S. Appl. No. 16/832,318, dated Nov. 3, 2021, 22 pages, U.S.
United States Patent and Trademark Office, Final Office Action received for U.S. Appl. No. 16/792,413, dated Jan. 10, 2022, 80 pages, U.S.
United States Patent and Trademark Office, Non-Final Office Action received for U.S. Appl. No. 16/792,413, dated Aug. 5, 2021, 32 pages, U.S.
United States Patent and Trademark Office, Non-Final Office Action received for U.S. Appl. No. 15/085,166, dated Jan. 10, 2022, 12 pages, U.S.
United States Patent and Trademark Office, Non-Final Office Action received for U.S. Appl. No. 16/867,286, dated Feb. 22, 2022, 38 pages, U.S.
United States Patent and Trademark Office, Non-Final Office Action received for U.S. Pat. No. 17,012,565, dated Apr. 12, 2022, 19 pages, U.S.A.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 17/144,426, dated May 31, 2022, 42 pages, US.
United States Patent and Trademark Office, Non-Final Office Action received for U.S. Appl. No. 16/832,318, dated Jun. 8, 2022, 17 pages, US.
United States Patent and Trademark Office, Notice of Allowability received for U.S. Appl. No. 15/422,184, filed Nov. 16, 2020, 2 pages, U.S.A.
United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
United States Patent and Trademark Office, Notice of Allowance received for U.S. Appl. No. 15/422,184, filed Oct. 13, 2020, 12 pages, U.S.A.
United States Patent and Trademark Office, Notice of Allowance received for U.S. Appl. No. 15/925,948, filed Nov. 5, 2020, 22 pages, U.S.A.
United States Patent and Trademark Office, Notice of Allowance received for U.S. Appl. No. 15/085,166, dated Sep. 10, 2021, 21 pages, U.S.
United States Patent and Trademark Office, Notice of Allowance received for U.S. Appl. No. 15/085,166, dated Jun. 15, 2022, 18 pages, U.S.
United States Patent and Trademark Office, Notice of Allowance received for U.S. Appl. No. 17/092,705, dated Dec. 23, 2021, 42 pages, U.S.
United States Patent and Trademark Office, Notice of Allowance received for U.S. Appl. No. 16/043,401, dated Aug. 10, 2020, 9 pages, U.S.A.
United States Patent and Trademark Office, Notice of Allowance received for U.S. Appl. No. 17/219,526, dated Feb. 3, 2022, 48 pages, U.S.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
United States Patent and Trademark Office, Office Action for U.S. Appl. No. 15/925,011, filed Apr. 8, 2020, 17 pages, U.S.A.
United States Patent and Trademark Office, Office Action for U.S. Appl. No. 15/925,948, filed Mar. 23, 2020, 29 pages, U.S.A.
United States Patent and Trademark Office, Office Action received for U.S. Appl. No. 15/422,184, filed May 18, 2020, 31 pages, U.S.A.
United States Patent and Trademark Office, Office Action received for U.S. Appl. No. 15/925,011, filed Oct. 8, 2020, 8 pages, U.S.A.
Wisconsin Physicians Service (WPS) Insurance Corporation, "How to Read Your Explanation of Benefits Chart," Jun. 16, 2012.

(56) References Cited

OTHER PUBLICATIONS www.ncoil.org/news/DrugCards2.doc dated Apr. 2002, 5 pages.

Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.

American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.

California Health Care Foundation, "When the Price Is Not Right: State Options on Prescription Drug Pricing", dated Jun. 2016, retrieved from the Internet at: <URL: https://www.chcf.org/wp-content/uploads/2017/12/PDF-WhenStateRxPricing.pdf>, 16 pages.

Hsee, Christopher K., et al., "General Evaluability Theory", Perspectives on Psychological Science, Jul. 2010, pp. 343-355, vol. 5, No. 4, Sage Publications, Inc. on behalf of the Association for Psychological Science retrieved from the Internet at <URL: https://www.jstor.org/stable/41613442>.

United States Patent and Trademark Office, Advisory Action received for U.S. Appl. No. 16/867,286, dated Dec. 6, 2022, 8 pages, US.

United States Patent and Trademark Office, Advisory Action received for U.S. Appl. No. 17/175,939, dated Dec. 22, 2022, 5 pages, US.

United States Patent and Trademark Office, Final Office Action received for U.S. Appl. No. 17/144,426, dated Dec. 8, 2022, 21 pages, US.

United States Patent and Trademark Office, Notice of Allowance received for U.S. Appl. No. 16/832,318, dated Dec. 8, 2022, 26 pages, US.

Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retrieved from the Internet at <URL: https://healthpolicy.usc.edu/research/prescription-drug-copayment-coupon-landscape/>, 21 pages.

United States Patent and Trademark Office, Advisory Action received for U.S. Appl. No. 16/867,286, dated Feb. 6, 2023, 3 pages, US.

United States Patent and Trademark Office, Advisory Action received for U.S. Appl. No. 17/144,426, dated Mar. 3, 2023, 6 pages, US.

United States Patent and Trademark Office, Final Office Action received for U.S. Appl. No. 17/158,118, dated Mar. 3, 2023, 19 pages, US.

United States Patent and Trademark Office, Notice of Allowance received for U.S. Appl. No. 16/552,021, dated Oct. 20, 2022, 14 pages, U.S.

United States Patent and Trademark Office, Final Office Action received for U.S. Appl. No. 16/816,460, dated Aug. 10, 2023, 14 pages, U.S.

United States Patent and Trademark Office, Non-Final Office Action received for U.S. Appl. No. 17/144,426, dated Jul. 13, 2023, 17 pages, U.S.

United States Patent and Trademark Office, Non-Final Office Action received for U.S. Appl. No. 17/158,118, dated Jul. 13, 2023, 18 pages, U.S.

United States Patent and Trademark Office, Advisory Action received for U.S. Appl. No. 17/144,426, dated Mar. 21, 2024, 5 pages.

United States Patent and Trademark Office, Advisory Action received for U.S. Appl. No. 17/674,366, dated Mar. 22, 2024, 6 pages.

United States Patent and Trademark Office, Final Office Action received for U.S. Appl. No. 17/705,919, dated Feb. 28, 2024, 61 pages.

United States Patent and Trademark Office, Final Office Action received for U.S. Appl. No. 17/175,939, dated Mar. 1, 2024, 24 pages.

United States Patent and Trademark Office, Non-Final Office Action received for U.S. Appl. No. 17/846,373, dated Apr. 5, 2024, 76 pages.

U.S. Appl. No. 16/816,460, "Adaptive System and Method for Adjudicating Claims to Reduce Member Responsibility", Unpublished (Filing Date Mar. 12, 2020), (Michael Rea, Inventor), (RC Savings, LLC, Assignee).

United States Patent and Trademark Office, Non-Final Office Action received for U.S. Appl. No. 16/816,460, dated Mar. 3, 2023, 14 pages, U.S.

United States Patent and Trademark Office, Final Office Action received for U.S. Appl. No. 17/162,461, dated May 19, 2023, 23 pages, U.S.

United States Patent and Trademark Office, Advisory Action received for U.S. Appl. No. 17/158,118, dated May 26, 2023, 5 pages, U.S.

United States Patent and Trademark Office, Non-Final Office Action received for U.S. Appl. No. 17/674,366, dated Jun. 6, 2023, 75 pages, U.S.

United States Patent and Trademark Office, Miscellaneous Office Action, Restarting Period, received for U.S. Appl. No. 17/175,939, dated Jun. 14, 2023, 23 pages, U.S.

Viswanthan, Meera, et al., "Interventions to Improve Adherence to Self-administered Medications for Chronic Diseases in the United States," Annals of Internal Medicine, Dec. 4, 2012, retrieved from the Internet at <https://www.acpjournals.org/doi/full/10.7326/0003-4819-157-11-201212040-00538?rfr_dat=cr_pub++0pubmed&url_ver=Z39.88-2003&rfr_id=ori%3Arid%3Acrossref.org> on Jun. 14, 2023, 25 pages.

United States Patent and Trademark Office, Final Office Action received for U.S. Appl. No. 17/012,565, dated Jul. 25, 2022, 43 pages, U.S.

United States Patent and Trademark Office, Advisory Action received for U.S. Appl. No. 17/162,461, dated Aug. 24, 2023, 2 pages, US.

United States Patent and Trademark Office, Final Office Action received for U.S. Appl. No. 16/867,286, dated Sep. 19, 2023, 16 pages, US.

United States Patent and Trademark Office, Advisory Action received for U.S. Appl. No. 16/816,460, dated Oct. 19, 2023, 3 pages, US.

United States Patent and Trademark Office, Non-Final Office Action received for U.S. Appl. No. 17/162,461, dated Oct. 19, 2023, 25 pages, US.

United States Patent and Trademark Office, Non-Final Office Action received for U.S. Appl. No. 16/867,286, dated Mar. 31, 2023, 16 pages, US.

United States Patent and Trademark Office, Non-Final Office Action received for U.S. Appl. No. 17/175,939, dated Apr. 26, 2023, 24 pages, US.

United States Patent and Trademark Office, Non-Final Office Action received for U.S. Appl. No. 17/705,919, dated Aug. 17, 2023, 68 pages, US.

United States Patent and Trademark Office, Final Office Action received for U.S. Appl. No. 17/674,366, dated Dec. 15, 2023, 53 pages, US.

United States Patent and Trademark Office, Final Office Action received for U.S. Appl. No. 17/144,426, dated Dec. 19, 2023, 22 pages, US.

United States Patent and Trademark Office, Final Office Action received for U.S. Appl. No. 17/158,118, dated Dec. 19, 2023, 22 pages, US.

United States Patent and Trademark Office, Non-Final Office Action received for U.S. Appl. No. 16/816,460, dated Dec. 22, 2023, 46 pages, US.

United States Patent and Trademark Office, Final Office Action received for U.S. Appl. No. 16/816,460, dated May 3, 2024, 22 pages, U.S.

United States Patent and Trademark Office, Non-Final Office Action received for U.S. Appl. No. 17/675,616, dated May 8, 2024, 74 pages, U.S.

United States Patent and Trademark Office, Advisory Action received for U.S. Appl. No. 16/816,460, dated Aug. 1, 2024, 3 pages, U.S.

United States Patent and Trademark Office, Advisory Action received for U.S. Appl. No. 17/162,461, dated Aug. 19, 2024, 2 pages, U.S.

United States Patent and Trademark Office, Non-Final Office Action received for U.S. Appl. No. 18/098,150, dated Aug. 27, 2024, 61 pages, U.S.

United States Patent and Trademark Office, Interview Summary received for U.S. Appl. No. 17/675,616, dated Aug. 15, 2024, 8 pages, U.S.

(56) References Cited

OTHER PUBLICATIONS

United States Patent and Trademark Office, Non-Final Office Action received for U.S. Appl. No. 17/674,366, dated Jun. 5, 2024, 54 pages, US.

United States Patent and Trademark Office, Final Office Action received for U.S. Appl. No. 17/162,461, dated Jun. 4, 2024, 38 pages, US.

Coase, R. H., "The Nature of the Firm", Economica, Nov. 1937, pp. 386-405, vol. 4, No. 16, Blackwell Publishing for London School of Economics and Political Science, retrieved from the Internet at http://www.jstor.org/stable/2626876 on Nov. 7, 2011.

Gemmill, Marin, "The price elasticity of demand for prescription drugs: an exploration of demand in different settings", Doctor of Philosophy Thesis submitted to the London School of Economics and Political Science, Jan. 2008, 380 pages, UMI No. U615895, UMI Dissertation Publishing, ProQuest LLC, US.

United States Patent and Trademark Office, Advisory Action and Examiner-Initiated Interview Summary received for U.S. Appl. No. 17/705,919, dated Jun. 25, 2024, 33 pages, US.

United States Patent and Trademark Office, Examiner's Answer received for U.S. Appl. No. 16/867,286, dated Jun. 28, 2024, 9 pages, US.

United States Patent and Trademark Office, Non-Final Office Action received for U.S. Appl. No. 17/144,426, dated Jul. 18, 2024, 19 pages, US.

United States Patent and Trademark Office, Non-Final Office Action received for U.S. Appl. No. 17/158,118, dated Jul. 18, 2024, 22 pages, US.

United States Patent and Trademark Office, Notice of Allowance received for U.S. Appl. No. 17/846,373, dated Jul. 25, 2024, 16 pages, US.

United States Patent and Trademark Office, Notice of Allowance received for U.S. Appl. No. 17/705,919, dated Sep. 3, 2024, 13 pages, USA.

United States Patent and Trademark Office, Notice of Allowance received for U.S. Appl. No. 17/675,616, dated Sep. 25, 2024, 21 pages, USA.

United States Patent and Trademark Office, Examiner Interview Summary received for U.S. Appl. No. 17/144,426, dated Oct. 22, 2024, 8 pages, U.S.

United States Patent and Trademark Office, Examiner Interview Summary received for U.S. Appl. No. 17/158,118, dated Oct. 22, 2024, 8 pages, U.S.

United States Patent and Trademark Office, Non-Final Office Action received for U.S. Appl. No. 17/501,532, dated Oct. 17, 2024, 37 pages, U.S.

United States Patent and Trademark Office, Non-Final Office Action received for U.S. Appl. No. 17/499,976, dated Oct. 1, 2024, 79 pages, U.S.

United States Patent and Trademark Office, Non-Final Office Action received for U.S. Appl. No. 17/175,939, dated Oct. 24, 2024, 17 pages, U.S.

United States Patent and Trademark Office, Examiner Interview Summary received for U.S. Appl. No. 18/098,150, dated Nov. 18, 2024, 3 pages, U.S.

United States Patent and Trademark Office, Non-Final Office Action received for U.S. Appl. No. 16/816,460, dated Nov. 21, 2024, 28 pages, US.

United States Patent and Trademark Office, Examiner Interview Summary received for U.S. Appl. No. 17/175,939, dated Dec. 3, 2024, 2 pages, US.

United States Patent and Trademark Office, Final Office Action received for U.S. Appl. No. 17/144,426, dated Dec. 19, 2024, 22 pages, U.S.

United States Patent and Trademark Office, Final Office Action received for U.S. Appl. No. 17/158,118, dated Dec. 19, 2024, 24 pages, US.

\* cited by examiner

METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION

CROSS REFERENCE TO RELATED APPLICATION

This application is a continuation-in-part of, and claims priority to U.S. patent application Ser. No. 16/792,413 filed Feb. 17, 2020, and entitled METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION, the entire contents of which is hereby incorporated by reference.

TECHNOLOGICAL FIELD

Embodiments of the present invention relate generally to prescription transactions and, more particularly, to methods, apparatuses, and computer program products for partitioning prescription transaction costs in an electronic prescription transaction, by determining a credit amount to be applied to an adjudicated prescription claim.

BACKGROUND

Some pharmaceutical manufacturers offer rebates, copay assistance, or credits toward the purchase of certain prescription drugs, to encourage patients to adhere to their prescription, provide patient support, compete against other branded drugs and alternative medications, and/or the like. In many instances a rebate can be used in addition to a patient's prescription benefit plan.

In some instances, a service provider computer may be authorized by a pharmaceutical manufacturer to distribute rebates, or credits, toward the cost of prescription drugs, as the service provider determines such that some transactions and/or patient may receive different rebate amounts, even for the same prescription drug. The variance between rebate amounts may be influenced by a variety of factors, including but not limited to pricing models to determine improved probability of prescription adherence, and/or the like. The service provider computer may automatically determine credit amounts in real-time or near real-time as prescription transactions and inquiries and submitted via a pharmacy.

In some jurisdictions, legislation may require that the price of prescription drugs under a government sponsored plan, such as Medicare Part D and/or the like, may not exceed the price of the same prescription drug under a commercial prescription plan. In some instances, the rebates or credits given by pharmaceutical manufacturers may not be applied when enforcing legislation that government sponsored plans receive the best price for a prescription drug, such that the manufacturers and/or service providers may liberally distribute credit or rebates without concern for violating legislation relating to pricing. However, new legislation has been proposed that may require service providers, manufacturers, and/or the like to ensure the cost of prescription drugs for a commercial payer, when taking into consideration any rebates applied or further patient assistance, is not less than the cost of the same drug for a government sponsored plan.

BRIEF SUMMARY

Methods, apparatuses, and computer program products are therefore provided for partitioning costs of prescription transactions by determining a credit amount to be applied to an adjudicated prescription claim.

An apparatus is provided, comprising at least one processor and at least one memory including computer program code, the at least one memory and the computer program code configured to, with the processor, cause the apparatus to at least receive, from a pharmacy computer, an indication of a prescription transaction comprising a patient identifier identifying a patient and a prescription identifier identifying a drug. The at least one memory and the computer program code are configured to, with the processor, cause the apparatus to determine an alternative cost of the drug available via an alternative system, and transmit a prescription claim associated with the prescription transaction to an adjudication computer. The at least one memory and the computer program code are further configured to, with the processor, cause the apparatus to receive an adjudicated prescription claim associated with the prescription transaction, the adjudicated prescription claim comprising a co-pay amount, and determine a preliminary remaining patient pay amount. The at least one memory and the computer program code are further configured to, with the processor, cause the apparatus to determine a preliminary credit amount as the co-pay amount minus the preliminary remaining patient pay amount. The at least one memory and the computer program code are further configured to, with the processor, cause the apparatus to determine that the preliminary credit amount would result in a payer cost that is lower than the alternative cost of the drug available via the alternative system.

The at least one memory and the computer program code are further configured to, with the processor, cause the apparatus to, in response to determining that the preliminary credit amount would result in a payer cost that is lower than the alternative cost of the drug available via the alternative system, adjust the preliminary credit amount to a credit amount that would result in a payer cost that is greater than or equal to the alternative cost. The at least one memory and the computer program code are further configured to, with the processor, cause the apparatus to determine the remaining patient pay amount by applying the credit amount, and reformat the adjudicated prescription claim to a format that includes the remaining patient pay amount and the credit amount, and that is readable by the pharmacy computer. The at least one memory and the computer program code are further configured to, with the processor, cause the apparatus to cause transmission of the adjudicated prescription claim including the remaining patient pay amount and the credit amount to the pharmacy computer.

The alternative cost of the drug may be determined by accessing historical data. The preliminary credit amount may be calculated according to a pricing model. The preliminary credit amount may be calculated in order to improve adherence rates. The alternative system is a government funded system. The at least one memory and the computer program code are further configured to, with the processor, cause the apparatus to at least cause transmission of the credit amount to at least one of the pharmacy computer or a third party computer.

A method is provided, including receiving, from a pharmacy computer, an indication of a prescription transaction comprising a patient identifier identifying a patient and a prescription identifier identifying a drug, and determining an alternative cost of the drug available via an alternative system. The method further includes transmitting a prescription claim associated with the prescription transaction to an adjudication computer, and receiving an adjudicated prescription claim associated with the prescription transaction, the adjudicated prescription claim comprising a co-pay amount. The method further includes determining a preliminary remaining patient pay amount, and determining a preliminary credit amount as the co-pay amount minus the preliminary remaining patient pay amount. The method may further include determining that the preliminary credit amount would result in a payer cost that is lower than the alternative cost of the drug available via the alternative system. In response to determining that the preliminary credit amount would result in a payer cost that is lower than the alternative cost of the drug available via the alternative system, the method includes adjusting the preliminary credit amount to a credit amount that would result in a payer cost that is greater than or equal to the alternative cost. The method further includes determining the remaining patient pay amount by applying the credit amount, reformatting the adjudicated prescription claim to a format that includes the remaining patient pay amount and the credit amount, and that is readable by the pharmacy computer, and causing transmission of the adjudicated prescription claim including the remaining patient pay amount and the credit amount to the pharmacy computer. The method may further include causing transmission of the credit amount to at least one of the pharmacy computer or a third party computer.

A computer program product comprising at least one non-transitory computer-readable storage medium having computer-executable program code instructions stored therein, the computer-executable program code instructions comprising program code instructions to receive, from a pharmacy computer, an indication of a prescription transaction comprising a patient identifier identifying a patient and a prescription identifier identifying a drug, and to determine an alternative cost of the drug available via an alternative system. The computer-executable program code instructions further include program code instructions to transmit a prescription claim associated with the prescription transaction to an adjudication computer, and receive an adjudicated prescription claim associated with the prescription transaction, the adjudicated prescription claim comprising a co-pay amount. The computer-executable program code instructions further include program code instructions to determine a preliminary remaining patient pay amount, and determine a preliminary credit amount as the co-pay amount minus the preliminary remaining patient pay amount. The computer-executable program code instructions further include program code instructions to determine that the preliminary credit amount would result in a payer cost that is lower than the alternative cost of the drug available via the alternative system. The computer-executable program code instructions further include program code instructions to, in response to determining that the preliminary credit amount would result in a payer cost that is lower than the alternative cost of the drug available via the alternative system, adjust the preliminary credit amount to a credit amount that would result in a payer cost that is greater than or equal to the alternative cost, and to determine the remaining patient pay amount by applying the credit amount. The computer-executable program code instructions further include program code instructions to reformat the adjudicated prescription claim to a format that includes the remaining patient pay amount and the credit amount, and that is readable by the pharmacy computer, and to cause transmission of the adjudicated prescription claim including the remaining patient pay amount and the credit amount to the pharmacy computer. The computer-executable program code instructions further include program code instructions to cause transmission of the credit amount to at least one of the pharmacy computer or a third party computer.

An apparatus is provided, with means for receiving, from a pharmacy computer, an indication of a prescription transaction comprising a patient identifier identifying a patient and a prescription identifier identifying a drug, and means for determining an alternative cost of the drug available via an alternative system. The apparatus further includes means for transmitting a prescription claim associated with the prescription transaction to an adjudication computer, and means for receiving an adjudicated prescription claim associated with the prescription transaction, the adjudicated prescription claim comprising a co-pay amount. The apparatus further includes means for determining a preliminary remaining patient pay amount, and means for determining a preliminary credit amount as the co-pay amount minus the preliminary remaining patient pay amount. The apparatus may further include means for determining that the preliminary credit amount would result in a payer cost that is lower than the alternative cost of the drug available via the alternative system. In response to determining that the preliminary credit amount would result in a payer cost that is lower than the alternative cost of the drug available via the alternative system, the apparatus includes means for adjusting the preliminary credit amount to a credit amount that would result in a payer cost that is greater than or equal to the alternative cost. The apparatus further includes means for determining the remaining patient pay amount by applying the credit amount, and means for reformatting the adjudicated prescription claim to a format that includes the remaining patient pay amount and the credit amount, and that is readable by the pharmacy computer, and causing transmission of the adjudicated prescription claim including the remaining patient pay amount and the credit amount to the pharmacy computer. The apparatus may further include causing transmission of the credit amount to at least one of the pharmacy computer or a third party computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
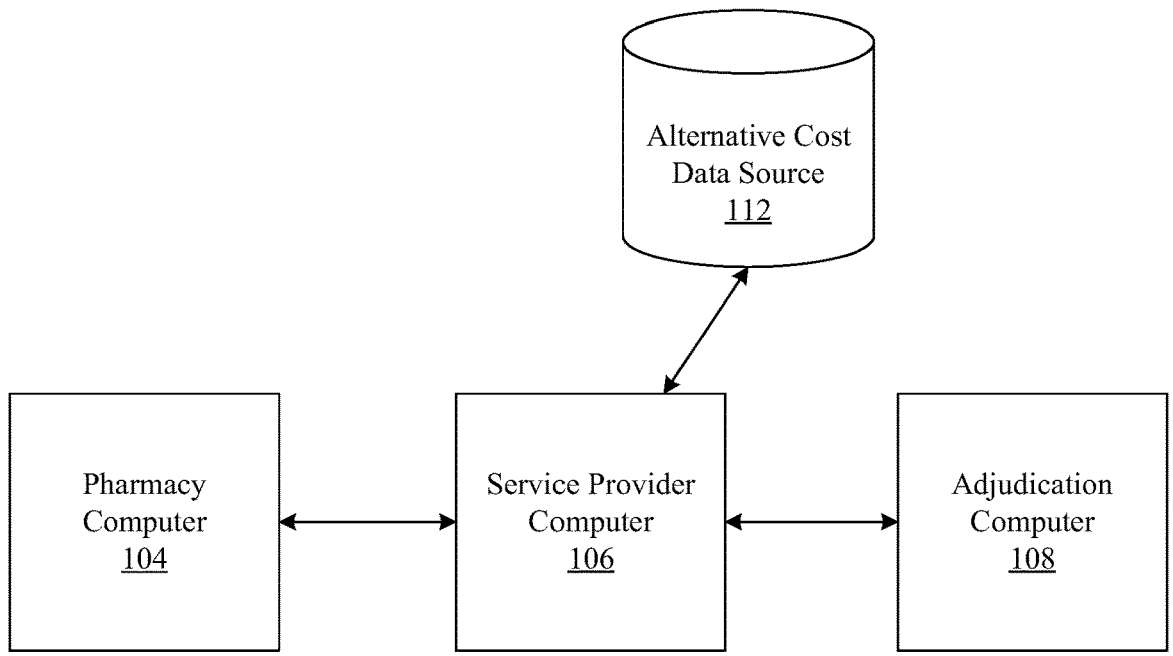
Figure 2:
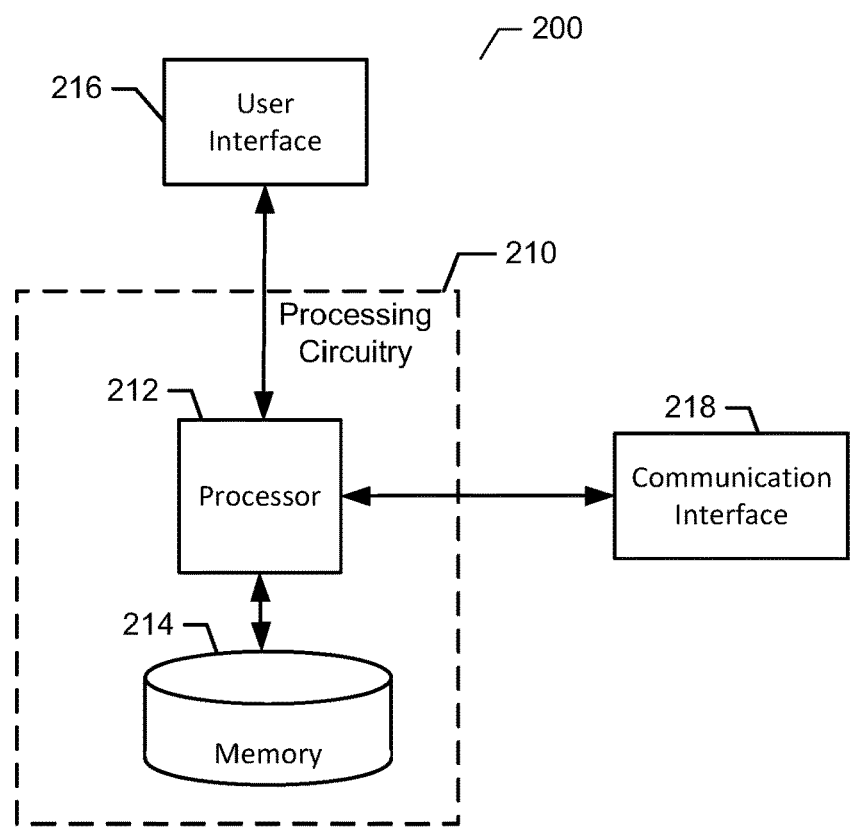
Figure 3:
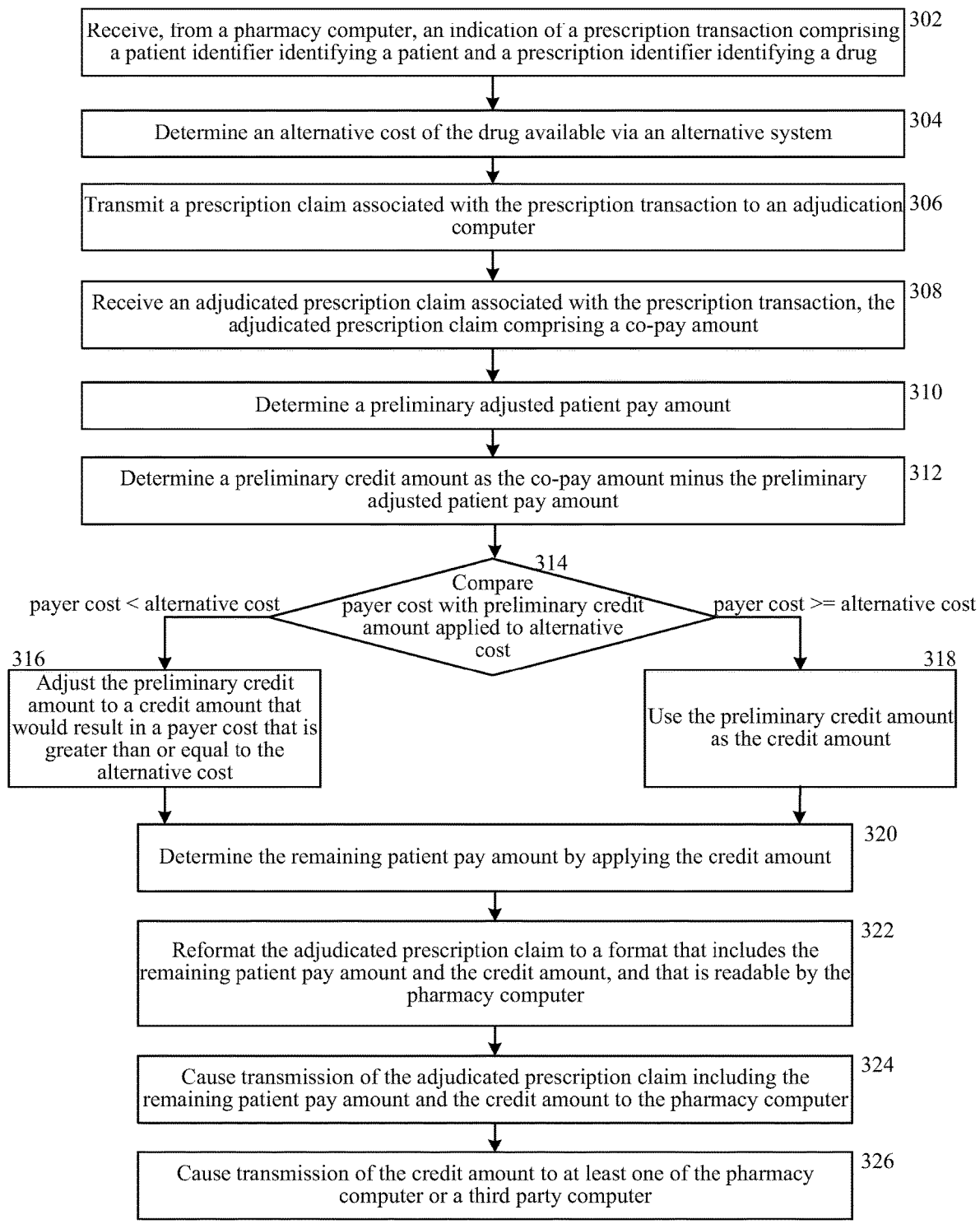

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIG. 3 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to partition prescription transaction costs by determining a credit amount to be applied to an adjudicated prescription claim, and according to certain example embodiments described herein. The pharmacy computer 104 may be associated with a pharmacy or pharmacy network to facilitate the filling of prescriptions, transmitting prescription claims to a service provider computer 106, and/or the like. The pharmacy computer 104 may additionally or alternatively be associated with a physician's office, clinic, long-term care facility, hospital, etc. Accordingly, while the exemplary pharmacy computer 104 may be frequently referenced herein as part of a pharmacy or pharmacy network, the pharmacy computer 104 may be associated with any other healthcare provider, such as a physician's office, hospital and/or other medical facility.

The pharmacy computer 104 may be any processor-driven device that facilitates the submission of prescription transaction requests made by patients or consumers and the communication of information associated with prescription transactions to the service provider computer 106. In certain example embodiments, the pharmacy computer 104 may be a point of sale device associated with a pharmacy. The execution of the computer-implemented instructions by the pharmacy computer 104 may form a special purpose computer or other particular machine that is operable to facilitate the submission of pharmacy transaction requests made by patients, pharmacists, and/or the like, and the communication of information associated therewith to a service provider computer 106.

The service provider computer 106 may include, but is not limited to, a processor-driven device that is configured for receiving, processing, and fulfilling prescription requests from the pharmacy computer 104 and/or the adjudication computer 108 (described below), relating to prescription tracking, claims processing, benefits, billing, other healthcare transactions, and/or other related activities. Additionally or alternatively, the service provider computer 106 may be operable to facilitate the receipt, routing, and/or processing of healthcare transactions such as prescription transactions, prescription claims, and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes healthcare transactions such as prescription transactions. For example, the service provider computer 106 may route prescription transactions communicated from the pharmacy computer 104 to an adjudication computer 108, such as that associated with a pharmacy benefits manager (PBM), an insurer, and/or other payer. According to certain embodiments, the adjudication computer 108 may comprise any other computer system that receives and adjudicates a prescription claim on behalf of the payer.

Additionally or alternatively, the service provider computer 106 may reformat healthcare transactions into another form of transaction and modify the recipient information of the reformatted transaction before routing the reformatted transaction to another party, such as adjudication computer 108. The service provider computer 106 may also optionally apply edits to at least some of the healthcare transactions.

The service provider computer 106 may transmit responses from the adjudication computer 108 regarding the prescription transaction to the pharmacy computer 104. For example, the service provider computer 106 may notify the pharmacy computer 104 of a co-pay or out of pocket costs to be paid by the patient for the prescription and/or the benefit applied to the prescription transaction. In this regard, a message or other notification may be appended to or included in the response transmitted to the pharmacy computer 104. Any of the aforementioned responses may be provided to the pharmacy computer 104 together with a prescription transaction response, or the service provider computer 106 may reformat the prescription transaction to include the details of such responses, and transmit the reformatted healthcare transaction back to the pharmacy computer 104.

The service provider computer 106 may be further configured, as authorized by a pharmaceutical manufacturer, to distribute rebates, or credits, toward the cost of prescription drugs, funded by the manufacturer, and calculated as the service provider determines such that some transactions and/or patient may receive different rebate amounts, even for the same prescription drug. In this regard, the service provider computer 106 may be configured to leverage transactions routed to and from the service provider computer 106 and relating to different prescription drugs, obtained at different pharmacies by different patients, and transmitted to various payers, prescription plans, adjudicators, and/or the like. The service provider computer 106 may create and maintain a pricing model that predicts prescription adherence based on prior transactions, reversals, and/or the like. The service provider computer 106 may utilize the pricing model to determine how to distribute credits or rebates funded by the pharmaceutical manufacturer. The pricing model can be updated with additional transactions over time to account for changes in pricing of drugs, changes in adherence trends, and/or the like. Such a model may therefore automatically discover trends for new drugs released to market, and understand consumer habits and price sensitivity with respect to prescription adherence and/or abandonment.

A pricing model implemented by the service provider computer 106 may be configured in a variety of ways to work toward one or more targets or objectives. For example, a pricing model may be used to smooth patient pay amounts of a prescription drug across different prescription benefit plans such that the pricing is more consistent between different plans. A pricing model may additionally or alternatively be configured to improve affordability and/or adherence in certain geographic locations and/or for certain prescription drugs and/or prescription drug categories. The pricing model may be implemented with many variations, and is discussed in further detail herein.

The service provider computer 106 may utilize the pricing model to determine a credit amount, funded from a pharmaceutical manufacturer and calculated by the service provider computer, as the pharmaceutical manufacturer agrees to allow the service provider computer to allocate credits for certain drugs amongst different patients and/or prescription transactions. According to certain examples, the credit amount may be considered a voucher, e-voucher, savings, instant savings, and/or the like, and may be calculated in real-time, near real-time, and/or on a per-transaction basis.

Proposed legislation may set forth a requirement that the determined cost to a commercial sponsor of a plan, such as a an employer-sponsor health plan, when considering any credits applied, may not be lower than what a government funded plan would pay for the same drug. Such requirements are sometimes referred to as a "best price guarantee," under which government plans should be guaranteed better (e.g., lower or equal) pricing on prescription drugs a commercial plan. Accordingly, example embodiments provided herein automatically determine and apply a credit amount such that the price paid by a commercial payer for a drug is not lower than a price paid by a government plan. In some scenarios, a prior implementation of automatic distribution of varied or differentiated credit amounts, calculated in real-time when a patient obtains a prescription, such as to improve drug affordability and adherence rates, creates a technical challenge in enforcing the best price guarantee. Example embodiments described herein address such challenges accordingly.

The alternative cost data source 112 may comprise any computing device configured to provide alternative pricing information to the service provider computer 106, such as alternative pricing available under a government sponsored plan, such as Medicare Part D, or other government healthcare insurance program payer. For example, the alternative cost data source 112 may be a system or database associated with a provider for government sponsored plans and/or a third party system configured to track pricing offered by government sponsored plans. According to certain embodiments, the alternative cost data source 112 may be maintained or operated by the pharmacy computer 104, such as in instances in which the pharmacy tracks historical data or historical pricing of transactions occurring at the pharmacy, including prices paid under government sponsored plans. In some embodiments, the alternative cost data source 112 may be maintained or operated by the service provider computer 106 as it functions as a switch and/or router of various types of pharmacy and medical claims. As yet another example, the contracted costs of certain drugs for the government sponsored plan may be provided to the alternative cost data source 112, such as via a pricing file and/or the like. According to certain embodiments, alternative costs for which a government sponsored plan may purchase drugs may include costs by formulary tier.

Referring now to FIG. 2, apparatus 200 is a computing device(s) configured for implementing pharmacy computer 104, service provider computer 106, adjudication computer 108, and/or alternative cost data source 112, according to example embodiments.

Apparatus 200 may at least partially or wholly embody or be embodied by any of the pharmacy computer 104, service provider computer 106, and/or adjudication computer 108. Apparatus 200 may therefore implement any of the pharmacy computer 104, service provider computer 106, and/or adjudication computer 108, in accordance with some example embodiments, or may be implemented as a distributed system that includes any of the pharmacy computer 104, service provider computer 106, and/or adjudication computer 108.

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the pharmacy computer 104 (such as when the pharmacy computer 104 is implemented as a service communicatively connected to a work station or other user device utilized by a pharmacist or other pharmacy employee), service provider computer 106, and/or adjudication computer 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the pharmacy computer 104, service provider computer 106, adjudication computer 108, alternative data source 112, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as pharmacy computer 104, service provider computer 106, adjudication computer 108, and/or apparatus 200. In some example embodiments, the processor 212 may be configured to execute instructions stored in the memory 214 or otherwise accessible to the processor 212.

As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a pharmacy computer 104, and/or adjudication computer 108. Memory 214 may further include reconciliation tables for tracking the healthcare transactions received from the pharmacy computer 104, and reconciling them with responses received from adjudication computer 108. The memory 214 may further comprise a database, such as alternative cost data source 112 comprising alternative costs such as under government plan. Still further, according to certain embodiments, the memory 214 may be modified as described herein, to reformat prescription claims and/or prescription transactions with additional information received, determined and/or generated according to example embodiments, such as determined credits amounts, and/or determined patient pay amounts.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the pharmacy computer 104, the user interface 216 may, in some example embodiments, provide means for user entry of insurance information, details relating to the dispensing of a prescription, and/or the like. The user interface 216 may be further configured to display or provide co-pay and/or out of pocket costs of prescription medications, such as when apparatus 200 is implemented as a pharmacy computer 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of pharmacy computer 104, service provider computer 106, adjudication computer 108, alternative cost data source 112, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., pharmacy computer 104, service provider computer 106, adjudication computer 108, alternative cost data source 112, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

FIG. 3 is a flowchart illustrating example operations of an apparatus 200, according to some example embodiments. The operations of FIG. 3 may be performed by apparatus 200, such as with the service provider computer 106, and/or the like.

As shown by operation 302, apparatus 200 may include means, such as processor 212, memory 214, communication interface 218, and/or the like, for receiving an indication of a prescription transaction comprising a patient identifier identifying a patient and a prescription identifier identifying a drug. The prescription transaction may be received from the pharmacy computer 104, such as following entry by a pharmacist or other user of data relating to a prescription drug being obtained by a patient. In this regard, the prescription transaction may include a prescription claim entered by a healthcare provider, such as a pharmacist, and may include one or more of the following information:

Payer ID/Routing Information
    Transaction Payer Identifier(s) that designates a destination of the healthcare transaction (e.g., BIN Number, BIN Number and PCN, or BIN Number and Group ID)
Transaction Code
Patient Information
    Name (e.g. Patient Last Name, Patient First Name, etc.)
    Date of Birth of Patient Age of Patient
Patient Gender Code
Patient Address (e.g. Street Address, Zip Code, etc.)
Patient Contact Information (e.g. patient telephone number, email address, etc.)
Patient Health Condition Information
Patient Identification Identifier (such as, but not limited to, patient social security number, a subset of the patient social security number, health insurance claim number (HICN), cardholder ID, etc.)
Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy or other Healthcare Provider Information (e.g. store name, chain identifier, etc.)
Pharmacy or other Healthcare Provider ID (e.g. NPI code)
Claim Information
Drug, service, or product information (e.g. via National Drug Code (NDC) number)
Prescription/Service Reference Number
Date Prescription Written
Quantity Dispensed
Days' Supply
Diagnosis/Condition
Pricing information for the drug/service/product
Number of Refills Authorized
One or more Drug Utilization (DUR) Codes
Date of Service
Intermediary Authorization Field The prescription transaction may be received at the service provider computer 106 for further processing as described below.

As shown by operation 304, apparatus 200 may include means, such as processor 212, memory 214, communication interface 218, and/or the like, for determining an alternative cost of the drug available via an alternative system. For example, example embodiments may access or receive an alternative cost for the drug that may be available to alternative payers, such as government sponsored plans including Medicare Part D and/or the like. The alternative cost available to the government payer may be referred to as a "best price," and may be calculated as the wholesale acquisition cost minus a contracted rebate amount, minus an administration fee and other fees. The alternative cost, rebate, and/or administration fees associated with the government payer may be accessed via the alternative cost data source 112, and/or may be determined in a variety of ways. According to certain embodiments, historical prices relating to prior prescription transactions may be stored, and used to predict future prices of the same prescription drug. In this regard, the historical prices may be maintained on the alternative cost data source 112 by the pharmacy, and/or provided from the pharmacy computer 104 to the service provider computer 106.

According to certain example embodiments, the service provider computer 106 may store and utilize historical prices from prior prescription transactions that were forwarded from the pharmacy computer 104 to the service provider computer 106 for adjudication. In this regard, the service provider computer 106 may function as or comprise an adjudication switch configured for receiving prescription transactions from the pharmacy computer 104 and routing the transactions accordingly. As such, some transactions may be forwarded to the adjudication computer 108, and/or some transactions covered under government plans may be forwarded to an administrator or payer of government plans. In certain embodiments, the adjudication computer 108 may be configured to adjudicate both claims under commercial plans and government plans. Transactions forwarded to an administrator or payer of government plans (and/or adjudication computer 108) may be stored, and a corresponding response received from the administrator, adjudication computer 108, and/or the like indicating an alternative cost under a government plan.

Example embodiments may return the alternative cost to the pharmacy computer 104 and/or store the alternative cost in the alternative cost data source 112. As such, the service provider computer 106 may maintain the alternative costs and utilize historical alternative costs to predict or determine the alternative cost of a particular prescription drug that a government sponsor may pay. In this regard, in certain embodiments, the alternative cost may be appended to the prescription transaction information, such as by the pharmacy computer 104, received by the service provider computer 106 as described with respect to operation 302.

In any event, example embodiments may receive the alternative price in real-time or near real-time responsive to the receipt of the prescription transaction, enabling a real-time or near real-time response to be provided to the pharmacy computer 104 as described in further detail below.

As used throughout, the terms real-time and near real-time indicate a seemingly instant response time at the pharmacy computer 104, such that a patient obtaining a prescription may obtain pricing information and the patient pay amount, as the pharmacist or other employee interacts with a user interface of the pharmacy computer 104 or a user interface in communication with the pharmacy computer 104. It will be appreciated that despite the reference to real-time or near real-time, certain delays based on computer processing time may be encountered.

Moreover, it will be appreciated that the alternative cost determined with respect to operation 304 may be referred to as a predicted alternative cost, or estimated alternative cost, due to certain embodiments utilizing historical data and/or other means to predict or estimate the alternative cost.

As shown by operation 306, apparatus 200 may include means, such as processor 212, memory 214, communication interface 218, and/or the like, for transmitting a prescription claim associated with the prescription transaction to an adjudication computer, such as adjudication computer 108. Example embodiments may access a routing table or other data to determine a recipient adjudication computer 108 to which to transmit a prescription claim. In this regard, example embodiments may generate the prescription claim from information provided in the prescription transaction, or forward the prescription transaction as a claim to the adjudication computer 108. The prescription claim may be transmitted to the adjudication computer 108 in real-time or near real-time in response to receiving the prescription transaction from the pharmacy computer 104, thereby enabling the service provider computer 106 to provide a response to the pharmacy computer 104 regarding out-ofpocket costs or patient pay amount, as described in further detail below, in real-time or near real-time.

Once received from the service provider computer 106, the adjudication computer 108 may process the prescription claim and generate a benefit response message. For example, the adjudication computer 108 may adjudicate the prescription claim, such as according to plan policies. The adjudication computer 108 may access prior claim details for the patient, and/or amounts previously paid by the patient to determine whether the deductible has been met. In this regard, the adjudication computer 108 may include in the benefit response message the benefit amount, co-pay, and/or remaining balance owed for the prescription identified in the prescription claim. The benefit, co-pay, or remaining balance may vary depending on whether the deductible is met, depending on agreed upon pricing for the medication under the plan, and/or the like. Other rules and/or requirements may be processed and/or validated to determine the benefit. The benefit response message may be appended to or incorporated with the prescription claim, such that when received by the service prover computer 106, the service provider computer 106 identifies the source of the response as associated with the originating prescription transaction received in operation 302. The processed, or adjudicated prescription claim, may be transmitted back to the service provider computer 106 as an adjudicated prescription claim.

Accordingly, in operation 308, apparatus 200 may include means, such as processor 212, memory 214, communication interface 218, and/or the like, to receive an adjudicated prescription claim associated with the prescription transaction, the adjudicated prescription claim comprising a co-pay amount. In this regard, the co-pay amount received in the adjudicated prescription claim may be considered an initial co-pay amount provided by the adjudication computer 108, but may, according to certain embodiments, be further reduced as set forth below. In this regard, the co-pay amount may not yet reflect any credit amount to be applied, because the credit amount may be determined by example embodiments, such as processor 212 of the service provider computer 106.

As shown by operation 310, apparatus 200 may include means, such as processor 212, memory 214, and/or the like, for determining a preliminary adjusted patient pay amount. For example, as described in U.S. patent application Ser. No. 16/792,413, a remaining patient pay amount that may be considered the preliminary patient pay amount according to example embodiments disclosed herein, may be calculated such that is equal to or less than a cash price for a drug available through a cash discount system. In this regard, certain example embodiments may be implemented such that the preliminary adjusted patient pay amount is equal to the cash price of the drug. As another example, the preliminary adjusted patient pay amount may be calculated such that it is a certain or predefined percent less than the cash price of the drug, for example, 5% less than the cash price. According to certain embodiments, the preliminary adjusted patient pay amount may be calculated such that it is a certain or predefined dollar amount less than the cash price of the drug, for example, $1 less than the cash price. Still further, in certain embodiments, a preliminary adjusted patient pay amount may be calculated as a certain percent or dollar amount less than the cash price, then rounded down to the nearest dollar.

As shown by operation 312, apparatus 200 may include means, such as processor 212, memory 214, and/or the like, for determining a preliminary credit amount as the co-pay amount minus the preliminary adjusted patient pay amount.

According to certain example embodiments, the preliminary credit amount and/or preliminary adjusted patient pay amount may be determined according to a pricing model maintained by the service provider computer 106. According to certain embodiments, various rules, formulas, or algorithms relating to the pricing model may be implemented in different scenarios and based on a variety of factors and/or objectives. For example, one objective may include to provide smoother, or more consistent pricing of a common prescription drug across different prescription benefit plans. Another objective may include to improve adherence and/or optimize adherence. For example, manufactures may have objectives that may be implemented for certain or limited time periods for example, to make certain prescription drugs, such as a new prescription drug more affordable.

As another example, a pricing model based on pricing sensitivity, adherence and/or abandonment, may indicate a percentage or ratio of abandonment (e.g., when the patient fails to purchase their prescription, or reverses an insurance claim, such as to utilize a cash discount system), for transactions reflecting a particular co-pay or patient pay amount or range thereof. Some pricing models may account for demographic information. For example, some locales such as high poverty areas may have greater sensitivity to price variance, whereas areas of lower poverty may have more stable adherence relative to price variance. Example embodiments may therefore be configured to distribute more credit towards transactions in geographic areas associated with higher poverty. Various factors or indicators may be incorporated into the model.

Regardless of implementation, example embodiments may utilize regression analysis, and/or any other analysis technique or process to determine a preliminary adjusted patient pay amount to use as a target, in an effort to increase or improve, the number of paid claims and/or completed transactions relative to completion of prior transactions. In this regard, a pricing model may be utilized to determine a preliminary adjusted patient pay amount, and therefore, the credit amount, and reduce the number of abandoned or reversed prescription claims. For example, processor 212 may determine the remaining patient pay amount, and therefore, the credit amount, to attempt to reach a goal of 98% (or any other goal) completed prescription claims, based on the price sensitivity model and regression analysis applied thereto. An improvement in adherence may be measured or determined based on a prediction of adherence without the credit applied, in comparison to a prediction of adherence with the credit applied. For example, a particular prescription drug without any credits applied may be associated with a predicted adherence rate of 85% when prescribed to a particular patient and/or demographic. The processor 212 may determine a credit amount that when applied, increases the predicted adherence rate to 98%, reflecting an improvement to an adherence rate.

In any event, as shown by the left branch of operation 314, apparatus 200 may include means, such as processor 212, memory 214, communication interface 218, and/or the like, to determine that the preliminary credit amount, if applied, would result in a payer cost, such as a commercial payer cost, that is lower than the alternative cost of the drug available via the alternative system, such as a government plan.

In such instances in which it is determined that the preliminary credit amount would result in a payer cost that is lower than the cost to a commercial payer, as shown by operation 316, apparatus 200 may include means, such as processor 212, memory 214, communication interface 218, and/or the like, for adjusting the preliminary credit amount to a credit amount that would result in a payer cost that is greater than or equal to the alternative cost. For example, the processor 212 of the service provider computer 106 may adjust the preliminary credit amount to a credit amount that would not result in a lower payer cost for commercial payers than for government sponsored payers. This may include, for example, raising the preliminary credit amount to a credit amount that results in the payer cost for the commercial payer matching the price for government sponsored payers.

If in operation 314 it is determined the payer cost with a preliminary credit amount applied would not be lower than the alternative cost, or cost for government payers, as shown by operation 318, the preliminary credit amount may not need to be adjusted, and can be used as the credit amount.

It will be appreciated that although the comparison in operation 314 is shown with resultant branches of "less than" and "greater than or equal to," any relationship between the payer cost and alternative cost may be contemplated, such as for example, "less than or equal to" and "greater than."

As shown by operation 320, apparatus 200 may include means, such as processor 212, memory 214, communication interface 218, and/or the like, for determining the remaining patient pay amount by applying the credit amount. In scenarios of the right branch from operation 314 occurs, including operation 318, the remaining patient pay amount may be the same as the preliminary remaining patient pay amount. However, in circumstances in which the left branch from operation 314 occurs, including operation 316, the remaining patient pay amount may be adjusted based on the adjusted credit amount. The processor 212 may be configured to calculate the remaining patient pay amount by subtracting the credit amount from the co-pay amount provided by the adjudication computer 108, for example. In scenarios in which target patient pay amounts were attempted to match or fall below cash prices but such reductions resulted in commercial payers paying less for a drug than government sponsored payers, the patient pay amount may be further adjusted based on the adjusted credit amount.

As shown by operation 322, apparatus 200 may include means, such as processor 212, memory 214, communication interface 218, and/or the like, for reformatting the adjudicated prescription claim to a format that includes the remaining patient pay amount and the credit amount, and that is readable by the pharmacy computer. In this regard, the fields reflecting the remaining patient pay amount, and credit amount, that reflect any adjustments described above, may be inserted into the adjudicated prescription claim.

As shown by operation 324, apparatus 200 may include means, such as processor 212, memory 214, communication interface 218, and/or the like, for causing transmission of the adjudicated prescription claim including the remaining patient pay amount and the credit amount to the pharmacy computer. The result may be an adjusted co-pay, or adjusted out-of-pocket cost to be transmitted to the pharmacy computer 104 for provision via a user interface, such that the remaining patient pay amount can be communicated to the patient. According to certain embodiments, the patient may be motivated to purchase the prescription rather than abandon the prescription such as due to a high cost. The patient may therefore benefit from affordable medication and may be encouraged to adhere to the prescription. In certain embodiments and scenarios, the patient may further benefit from application of the out of pocket cost toward the insurance plan deductible (and therefore possibly reduced future out of pocket costs), in comparison to purchase of the medication under the cash discount system, which may not be applied to the insurance plan deductible. The service provider computer 106 may provide such benefit in real-time or near real-time while abiding by any pricing restrictions, as may be set forth by certain legislation or other requirements.

As set forth above, example embodiments partition prescription transaction costs by determining a credit amount based on an adjudicated prescription claim from adjudication computer 108 (and a provided co-pay), and further based on alternative costs from an alternative cost data source 112. In certain example embodiments, as shown in operation 326, apparatus 200 may include means, such as processor 212, memory 214, communication interface 218, and/or the like, to cause transmission of the credit amount to at least one of the pharmacy computer or a third party computer. In this regard, the credit amount may be paid by another party, and/or reported to the pharmaceutical manufacturer for record keeping and/or the like.

Example embodiments provided herein therefore provide a technical solution to the technical problem presented by service provider computers that have implemented systems to automatically distribute or determine credit amounts toward prescription drugs, in real-time or near real-time as the patient attempts to obtain the drug, as a pharmacy submits a prescription claim or inquiry, as a prescriber enters a prescription and/or the like. The problem is routed in computer technology, as such systems enable real-time automated pricing of prescription drugs and/or associated credits, based on real-time information. The pricing of certain prescriptions may therefore vary over time, frequently, and automatically based on updates to the pricing model.

The network-based implementations provided by the service provider computer to enable real-time determination of rebates and drug pricing create an additional technical challenge when the service provider computer 106 facilitates enforcement of a best price guarantee for government plans. Intelligent and automated pricing systems that utilize pricing models to estimate target prices of prescription drugs promote affordability and encourage prescription adherence. However, such systems may violate legislation that enforces better pricing of prescription drugs for government sponsored plans over commercial plans. Example embodiments provided herein improve upon such automated pricing and/or calculation of credits by further enforcing pricing guarantees, therefore enabling continued use of such systems that could otherwise lead to pricing violations.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the at least one processor, cause the apparatus to at least:
   receive, at a service provider computer and from a pharmacy computer, an indication of a prescription transaction comprising a patient identifier identifying a patient and a prescription identifier identifying a drug; and
   in real-time or near real-time relative to receiving the indication of the prescription transaction, and by the service provider computer:
      access an alternative cost data source to determine an alternative cost of the drug available via an alternative system associated with a government-sponsored payer;
      transmit a prescription claim associated with the prescription transaction to an adjudication computer identified from a plurality of adjudication computers based on insurance information provided in the prescription transaction;
      receive an adjudicated prescription claim associated with the prescription transaction, the adjudicated prescription claim comprising a co-pay amount;
      determine a preliminary remaining patient pay amount by applying a predefined target adherence rate to a price sensitivity model;
      determine a preliminary credit amount as the co-pay amount minus the preliminary remaining patient pay amount determined by applying a predefined target adherence rate to the price sensitivity model;
      determine that the preliminary credit amount would result in a payer cost that is lower than the alternative cost of the drug available via the alternative system;
      in response to determining that the preliminary credit amount would result in a payer cost that is lower than the alternative cost of the drug available via the alternative system, adjust the preliminary credit amount by applying a predefined target adherence rate to the price sensitivity model, wherein the preliminary credit amount is adjusted to a credit amount that would result in a payer cost that is greater than or equal to the alternative cost;
      determine a remaining patient pay amount by applying the credit amount to the preliminary credit amount determined based on at least the price sensitivity model;
      in response to determining the remaining patient pay amount based at least on the price sensitivity model, reformat the adjudicated prescription claim to a format that includes the remaining patient pay amount and the credit amount, and that is readable by the pharmacy computer; and
      cause transmission of the adjudicated prescription claim including the remaining patient pay amount and the credit amount to the pharmacy computer.

2. The apparatus of claim 1, wherein the alternative cost of the drug is determined by accessing historical data.

3. The apparatus of claim 1, wherein the preliminary credit amount is calculated in order to improve adherence rates.

4. The apparatus of claim 1, wherein the alternative system is a government funded system.

5. The apparatus of claim 1, wherein the at least one memory and the computer program code are further configured to, with the at least one processor, cause the apparatus to at least:

cause transmission of the credit amount to at least one of the pharmacy computer or a third party computer.

6. A method comprising:
receiving, at a service provider computer and from a pharmacy computer, an indication of a prescription transaction comprising a patient identifier identifying a patient and a prescription identifier identifying a drug; and
in real-time or near real-time relative to receiving the indication of the prescription transaction, and by the service provider computer:
accessing an alternative cost data source to determine an alternative cost of the drug available via an alternative system associated with a government-sponsored payer;
transmitting a prescription claim associated with the prescription transaction to an adjudication computer identified from a plurality of adjudication computers based on insurance information provided in the prescription transaction;
receiving an adjudicated prescription claim associated with the prescription transaction, the adjudicated prescription claim comprising a co-pay amount;
determining a preliminary remaining patient pay amount by applying a predefined target adherence rate to a price sensitivity model;
determining a preliminary credit amount as the co-pay amount minus the preliminary remaining patient pay amount determined by applying a predefined target adherence rate to the price sensitivity model;
determining that the preliminary credit amount would result in a payer cost that is lower than the alternative cost of the drug available via the alternative system;
in response to determining that the preliminary credit amount would result in a payer cost that is lower than the alternative cost of the drug available via the alternative system, adjusting the preliminary credit amount by applying a predefined target adherence rate to the price sensitivity model, wherein the preliminary credit amount is adjusted to a credit amount that would result in a payer cost that is greater than or equal to the alternative cost;
determining a remaining patient pay amount by applying the credit amount to the preliminary credit amount determined based on at least the price sensitivity model;
in response to determining the remaining patient pay amount based at least on the price sensitivity model, reformatting the adjudicated prescription claim to a format that includes the remaining patient pay amount and the credit amount, and that is readable by the pharmacy computer; and
causing transmission of the adjudicated prescription claim including the remaining patient pay amount and the credit amount to the pharmacy computer.

7. The method of claim 6, wherein the alternative cost of the drug is determined by accessing historical data.

8. The method of claim 6, wherein the preliminary credit amount is calculated in order to improve adherence rates.

9. The method of claim 6, wherein the alternative system is a government funded system.

10. The method of claim 6, further comprising:
causing transmission of the credit amount to at least one of the pharmacy computer or a third party computer.

11. A computer program product comprising at least one non-transitory computer-readable storage medium having computer-executable program code instructions stored therein, the computer-executable program code instructions comprising program code instructions to:
receive, by a service provider computer and from a pharmacy computer, an indication of a prescription transaction comprising a patient identifier identifying a patient and a prescription identifier identifying a drug; and
in real-time or near real-time relative to receiving the indication of the prescription transaction:
access an alternative cost data source to determine an alternative cost of the drug available via an alternative system associated with a government-sponsored payer;
transmit a prescription claim associated with the prescription transaction to an adjudication computer identified from a plurality of adjudication computers based on insurance information provided in the prescription transaction;
receive an adjudicated prescription claim associated with the prescription transaction, the adjudicated prescription claim comprising a co-pay amount;
determine a preliminary remaining patient pay amount by applying a predefined target adherence rate to a price sensitivity model;
determine a preliminary credit amount as the co-pay amount minus the preliminary remaining patient pay amount determined by applying a predefined target adherence rate to the price sensitivity model;
determine that the preliminary credit amount would result in a payer cost that is lower than the alternative cost of the drug available via the alternative system;
in response to determining that the preliminary credit amount would result in a payer cost that is lower than the alternative cost of the drug available via the alternative system, adjust the preliminary credit amount by applying a predefined target adherence rate to the price sensitivity model, wherein the preliminary credit amount is adjusted to a credit amount that would result in a payer cost that is greater than or equal to the alternative cost;
determine a remaining patient pay amount by applying the credit amount to the preliminary credit amount determined based on at least the price sensitivity model;
in response to determining the remaining patient pay amount based at least on the price sensitivity model, reformat the adjudicated prescription claim to a format that includes the remaining patient pay amount and the credit amount, and that is readable by the pharmacy computer; and
cause transmission of the adjudicated prescription claim including the remaining patient pay amount and the credit amount to the pharmacy computer.

12. The computer program product of claim 11, wherein the alternative cost of the drug is determined by accessing historical data.

13. The computer program product of claim 11, wherein the preliminary credit amount is calculated in order to improve adherence rates.

14. The computer program product of claim 11, wherein the alternative system is a government funded system.

15. The computer program product of claim 11, wherein the computer-executable program code instructions further comprise program code instructions to:

cause transmission of the credit amount to at least one of the pharmacy computer or a third party computer.

\* \* \* \* \*